United States Patent [19]

Shihata

[11] Patent Number: 5,778,886
[45] Date of Patent: Jul. 14, 1998

[54] VAGINAL COMPOSITIONS COMBINING A SPERMICIDAL AGENT AND A PEROXYGEN COMPOUND

[76] Inventor: Alfred Shihata, 13565 Mira Montana Dr., Del Mar, Calif. 92014

[21] Appl. No.: 607,571

[22] Filed: Feb. 27, 1996

[51] Int. Cl.$^6$ ....................................... A61F 6/06
[52] U.S. Cl. ........................ 128/832; 424/430; 128/830
[58] Field of Search .................... 128/830–842; 424/430

[56] References Cited

U.S. PATENT DOCUMENTS

| | | |
|---|---|---|
| 4,858,624 | 8/1989 | Shihata . |
| 4,917,901 | 4/1990 | Bourbon .................................. 424/673 |
| 4,959,216 | 9/1990 | Daunter ................................... 128/832 |
| 4,989,618 | 2/1991 | Shihata . |
| 5,059,417 | 10/1991 | Williams et al. . |
| 5,207,232 | 5/1993 | Shihata . |
| 5,466,463 | 11/1995 | Ford .......................................... 424/433 |
| 5,536,743 | 7/1996 | Borgman ................................ 514/39.8 |

OTHER PUBLICATIONS

Femcap feminine cap Brochure.
Contraceptice Technology, (1994) 16th revised editionIrvington Publishers, Inc. New York.
Klebanoff, S., et al. (1991) Control of the microbial flora of the vagina by $H_2O_2$–generating lactobacilli. The Journal of Infectious Diseases 164:94–100.
Klebanoff, S., et al., (1974) Virucidal activity of $H_2O_2$–generating bacteria: requirement for peroxidase and a halide. The Journal of Infectous Diseases 129(3):345–348.
Klebanoff, S., et al. (1991) Viricidal effect of lactobacillus acidophilus on human immunodeficiency virus type 1: possible role in heterosexual transmission. J. Exp. Med. 174:289–292.
Roddy, R., et al. (1993) A dosing study of nonoxynol–9 and genital irritation. International Journal of STD & AIDS 4:165–170.
Voeller, B. Nonxynol–9 and HTLV–III. The Lancet, May 17, 1989 p. 1153.
Voeller, B. (1992) Spermicides for controlling the spread of HIV. AIDS 6(3):341–342.
Voeller, B., et al., (1992) Heterosexual transmission of HIV. Letters 267(14) 1917–1919.
Voeller, B., et al. (1992) pH and related factors in the urogenital tract and rectum that affect HIV–1 transmission. Mariposa Occasional Paper No. 16., The Mariposa Education and Research Foundation: Topanga, CA.

*Primary Examiner*—Michael A. Brown
*Attorney, Agent, or Firm*—Knobbe, Martens, Olson & Bear, LLP

[57] ABSTRACT

The invention provides vaginal compositions suitable for preventing conception and transmission of sexually transmitted diseases comprising a spermicidal agent and a peroxygen compound. Preferably, the spermicidal agent is nonoxynol-9. Also preferably, the peroxygen compound is hydrogen peroxide. The spermicidal agent is preferred at about 3% by weight. The peroxygen compound is also preferred at about 3% by weight. In other aspects, the invention provides these compositions at a pH of about 4, preferably about 3 or lower. This pH is favorably maintained with lactic acid. These compositions are preferably encapsulated in the form of a gel.

19 Claims, No Drawings

VAGINAL COMPOSITIONS COMBINING A SPERMICIDAL AGENT AND A PEROXYGEN COMPOUND

FIELD OF THE INVENTION

This invention relates to vaginal compositions suitable for preventing conception and transmission of sexually transmitted diseases combining a spermicidal agent and a peroxygen compound.

BACKGROUND OF THE INVENTION

Spermicidal compositions are useful for protection against pregnancy and sexually transmitted diseases. They can be used alone, with a mechanical barrier-type device (such as a diaphragm, cap, or sponge), or as an adjunct to other contraceptive methods (such as birth control pill, intra-uterine-device, or rhythm). These compositions generally contain a spermicidal chemical that kills sperm and a base or carrier, such as a foam, cream, gel, suppository, or tablet. Nonoxynol-9 and octoxynol are the only two spermicidal agents available in the United States. Both are surfactants that destroy the sperm cell membrane. Other surfactant products, including menfegol and benzalkonium chloride, are available in other parts of the world.

Spermicidal agents are also microbicides. They are lethal to microorganisms, including those that cause sexually transmitted diseases, such as gonorrhea, chlamydia, genital herpes, trichomonas, and syphilis. Spermicides are known to prevent transmission of these sexually transmitted diseases. While spermicides have been found to be toxic in vitro to HIV, the relationship between spermicide use and HIV risk is still not understood. Protection against sexually transmitted diseases is probably the most important noncontraceptive benefit of spermicide use, and, according to some studies, this protection extends to decreased risk of AIDS.

The use of spermicidal agents, however, is not without problems. These agents destroy the natural and safe ecology of the vagina. Due to their germicidal property, they kill the friendly bacteria—lactobacillus—that are essential for the health and non-pathogenic state of the vagina.

Lactobacillus bacteria produce hydrogen peroxide in the normal healthy vagina. Hydrogen peroxide acts as a topical antiseptic and cleansing agent. In vitro studies indicate it to be viricidal to the HIV virus. Its microbicidal effect is due to the release of oxygen, which also aids in the mechanical removal of adherent deposits from cavities and wounds.

U.S. Pat. No. 5,466,463 tried to solve the problem of the killing of lactobacillus bacteria in the vagina by spermicidal agents. (All references cited hereunder are incorporated herein by reference.) It described a vaginal suppository that contained the lactobacilli themselves in combination with a spermicide. These bacteria had to be freeze-dried and microencapsulated in order to protect them from the microbicidal action of the spermicide during the shelf-life of the suppository.

But this patent still presents problems. It is cumbersome to prepare the bacteria, freeze-dry them, and microencapsulate them for formulation with the spermicidal agent. There is also some question about how this invention can be considered operable when the spermicide is expected to kill the lactobacilli, due to its germicidal action, once the suppository is introduced into the vagina.

There remains, therefore, an urgent and compelling need for compositions containing a microbicidal spermicide to prevent conception and the transmission of sexually transmitted diseases and that solves the problem of the killing of the lactobacillus bacteria in the vagina by the spermicidal agent. With the magnitude of sexually transmitted diseases and the emergence of AIDS pandemically, the risk of life-threatening infection accompanying heterosexual activity is steadily increasing. These compositions would substantially decrease the risk of sexually transmitted diseases, including that caused by HIV.

Accordingly, it is an objective of the invention to provide intravaginal microbicidal spermicides that not only kill microbes and sperm, but also maintain the normal ecology of the vagina.

Another disadvantage of spermicides is that they can cause vaginal irritation, especially with frequent exposure or higher doses. Still another disadvantage is that they are easily absorbed by the vaginal wall and cervix. This necessitates reapplication with every act of intercourse. Such reapplication, especially when frequent or in high doses, causes irritation and even ulceration of the vaginal wall.

Intravaginal barrier-type devices are known to be useful for the prevention of conception. They tend to combine two contraceptive mechanisms, a physical barrier to shield the cervix and a chemical to kill the sperm. U.S. Pat. Nos. 4,858,624, 4,989,618, and 5,207,232 describe certain barrier-type devices that are designed also to hold the spermicide in place and to trap the sperm. These devices store and shield the spermicide from contact with the cervix and the wall of the vagina, thereby preventing irritation to, and absorbance by, the vaginal wall and cervix. These devices also act as a trap to sperm and microbes.

Another objective of the invention is accordingly to provide kits containing an intravaginal barrier-type device in combination with a microbicidal spermicide that solves the problem of the killing of the lactobacillus bacteria by the spermicidal agent. The device should block or shield the cervix from the direct and immediate entry of the ejaculate fluid, enhancing the effects of the microbicidal spermicide. The device should help to carry or hold the microbicidal spermicide, making it available for continuous release in the vagina. It should minimize the vaginal irritation by and absorption of the microbicidal spermicide. It should trap the sperm and microbes and thus increase their time of exposure to the microbicidal spermicide for a maximum killing effect. In this way, the combination of the chemical and physical barrier provides a double shield against conception and the invasion of microorganisms, including the HIV virus.

Further objectives of the invention are to stabilize the compositions described herein, to provide them in a suitable form, and to acidify the compositions to further kill sperm and microbes.

Still further objectives of the invention will become apparent from a consideration of the ensuing description.

SUMMARY OF THE INVENTION

In one aspect, the invention provides vaginal compositions suitable for preventing conception and transmission of sexually transmitted diseases comprising a spermicidal agent and a peroxygen compound. Preferably, the spermicidal agent is nonoxynol-9. Also preferably, the peroxygen compound is hydrogen peroxide. The spermicidal agent is preferred at about 3% by weight. The peroxygen compound is also preferred at about 3% by weight.

In other aspects, the invention provides these compositions at a pH of about 4, preferably about 3 or lower. This pH is favorably maintained with lactic acid. These compositions are preferably encapsulated in the form of a gel.

In still other aspects, the invention provides these compositions further comprising one or more of the following ingredients by weight: about 65–75% purified water, about 15–25% glycerin, about 1.0–5.0% polyacrylamide, C13–14 isoparaffin, and laureth-7, about 0.5–2.5% lactic acid, about 0.1–0.8% simethicone, about 0.1–0.5% potassium sorbate, about 0.1–0.3% methylparaben, and about 0.1–0.3% propylparaben.

The invention also includes kits adapted for barrier-type prevention of conception and transmission of sexually transmitted diseases comprising a barrier-type device and the vaginal compositions provided here.

The invention additionally encompasses methods of preventing conception and transmission of sexually transmitted diseases by applying intravaginally the compositions here described.

DETAILED DESCRIPTION OF THE PREFERRED EMBODIMENT

Vaginal compositions are provided in accordance with the present invention that combine a spermicidal agent with a peroxygen compound. These compositions meet the objectives of this invention, in that an intravaginal microbicidal spermicide is thus provided that not only kills microbes and sperm, but also is suited to the vaginal ecology by solving the problem of the killing of lactobacillus bacteria by the spermicidal agent. That is, an oxygen-supplying compound is provided to replace the loss of the oxygen generated in situ by $H_2O_2$ due to the death of the hydrogen peroxide-producing lactobacilli.

The components of these compositions attack microorganisms, including the HIV virus, using different approaches and through different mechanisms. For example, nonoxynol-9 is a detergent that acts to disrupt the cell membranes of microorganisms thereby killing them, and is fatal to other microorganisms in other ways. Peroxygen compounds produce nascent oxygen that kills microbes, including anaerobic bacteria, and other microorganisms, while the oxygen bubbles prevent the adherence of deposits on the vaginal wall that can form a breeding ground for microorganisms. These components kill sperm and pathogenic microorganisms in complementary fashions, while preserving the ecological environment of the vagina.

Further objectives of the invention are met by formulating the compositions in a gel form. Advantageously for chemical stability, the compositions are made acid pH. For added protection, the compositions are used in conjunction with mechanical barrier devices, such as those described in U.S. Pat. Nos. 4,858,624, 4,989,618, and 5,207,232.

Spermicidal Chamicals

Any spermicidal chemical is suitable for incorporation into the vaginal compositions of this invention, including nonoxynol-9 and octoxynol, which are the only two spermicidal agents available in the United States. Both are surfactants that destroy the sperm cell membrane. Other spermicides, whether acting as surfactants or through other mechanisms of action, are contemplated. For example, menfegol and benzalkonium chloride, which are spermicides and surfactants, and which are available in other parts of the world, are envisioned.

Spermicides that act to prevent transmission of one or more sexually transmitted diseases, such as gonorrhea, chlamydia, genital herpes, trichomonas, and syphilis, are part of the invention. Presumably they are lethal to agents that cause these diseases because they are surfactants, but other mechanisms of action are contemplated. It is advantageous that the microbicidal spermicides of the invention protect against the transmission of HIV, and decrease the risk of AIDS.

Nonoxynol-9 is the most commonly used spermicide in the United States due to its safety and efficacy, and is preferred. It is known to prevent the transmission of sexually transmitted diseases. In the laboratory, it is lethal to the HIV virus.

Peroxygen Compounds

A peroxygen compound is provided to supply oxygen, thus replacing the loss of the oxygen-generating hydrogen peroxide that is caused by the killing of the hydrogen peroxide-producing lactobacilli. A variety of water-soluble peroxygen compounds may be employed, such as sodium perborate, persilicate, perphosphate, and hydrogen peroxide. A preferred compound for this invention is hydrogen peroxide. In this case, the addition of hydrogen peroxide replaces the loss of the hydrogen peroxide-producing lactobacilli.

Formulations

The vaginal compositions of the invention combine a spermicidal agent with a peroxygen compound in a suitable form. These compositions generally contain the spermicidal chemical, the peroxygen compound, and a base or carrier, such as a foam, cream, gel, suppository, or tablet.

In preferred compositions, nonoxynol-9, or another spermicidal agent, is combined with hydrogen peroxide. Hydrogen peroxide, however, in the aqueous form and in neutral pH is very unstable and decomposes in a very short time. This instability quickly renders it useless.

To stabilize the hydrogen peroxide, it is preferably encapsulated as a gel and maintained at acid pH. For example, U.S. Pat. No. 5,059,417 describes an oral composition containing hydrogen peroxide that is stabilized by formulating it as a gel and maintaining it at a low pH. Advantageously for peroxide stability, the present compositions have a pH of about 4, preferably a pH of about 3 or lower. This high acidity is capable, by itself, of killing many microorganisms, including the HIV virus. The compositions of the invention therefore combine many different approaches to the prevention of transmission of sexually transmitted diseases, including AIDS. That is, the microbicidal spermicide, hydrogen peroxide, and pH of 4, or 3 or lower act in concert taking supplementary pathways to kill pathogenic microorganisms.

Concentrations, Amounts, and Percentages

The concentration of spermicidal chemical will vary depending on the base or carrier, but the amount will fall within the parameters of about 1% to about 28% by weight. At lower concentrations, there will not be enough spermicidal reagent to kill the sperm. At higher concentrations, the spermicidal chemical can irritate and even damage the vaginal epithelium. When the base or carrier is a gel, the spermicide concentration will range from about 1% to about 5% by weight. In this case, 3% by weight is preferred.

The amount of hydrogen peroxide will range from about 0.1% to about 10% by weight, advantageously about 1% to about 6% by weight, and optimally about 3% by weight. Hydrogen peroxide is widely used at 3% to disinfect open wounds and as a gargle and mouthwash. At this concentration, it is capable of killing anaerobes and other microorganisms, and of inactivating the HIV virus.

A chemically stable peroxide formulated gel is advantageously produced by maintaining a low pH, for example, a pH of about 4, preferably a pH of about 3 or lower. The lower end of the pH range will usually not be less than about 2. Acidification is achieved through use of any mild pharmaceutically acceptable acid, such as boric acid, or mild organic acids, such as lactic acid, ascorbic acid, citric acid, or acetic acid, optionally in combination with the respective sodium or other pharmaceutically acceptable salt, to the extent necessary to achieve the desired pH. Preferably lactic acid, optionally lactic acid with sodium lactate, is used for acidification.

In addition to the pharmacologically active compounds, the compositions of the present invention also contain certain non-essential ingredients. These ingredients are considered non-essential because the basic objectives of the invention can be attained without them. Nevertheless, the embodiments of the invention that include these non-essential ingredients offer certain advantages, and are therefore considered additional preferred embodiments.

Accordingly, preferred embodiments of the invention employ pharmacologically active compounds in admixture with certain excipients, i.e. pharmaceutically acceptable organic or inorganic carrier substances suitable for intravaginal application that do not deleteriously react with the active compounds. Suitable pharmaceutically acceptable carriers include but are not limited to water, salt solutions, alcohols, etc. The preparations of this invention can be sterilized and mixed with additional agents, like pharmaceutical excipients that make gel formulation possible. Other agents for admixture include, e.g., lubricants, preservatives, stabilizers, wetting agents, emulsifiers, and the like that do not deleteriously react with the active compounds.

The compositions of the invention are ideally designed to be water soluble, unscented, colorless, stainless, and greaseless. One such composition combines the following ingredients by weight: nonoxynol-9 (about 3%) and hydrogen peroxide (about 3%) with purified water (about 65%–75%) as a diluent and vehicle, glycerine (about 15%–25%) as a lubricant, polyacrylamide, C13–14 isoparaffin and laureth-7 (about 1.0%–5.0%) as gelling agent, lactic acid (about 0.5%–2.5%) for acidification, simethicone (about 0.1%–0.8%) as a defoamer, and potassium sorbate (about 0.1%–0.5%), methlyparaben (about 0.1%–0.3%), and propylparaben (about 0.1%–0.3%) as preservatives. In accelerated stability studies described in Example 2, this composition proved to be stable for as long as three years.

Dosages and Scheduling

As contraceptive gels, the compositions of this invention may be used with a mechanical barrier device, or used alone. One application of gel should provide 50 to 500 mg of spermicide, the preferred range being 80 to 150 mg, the preferred amount being 100 mg. Generally, the gel is applied using an applicator like those known in the art some time before each act of intercourse, and left in place for about 6–8 hours after intercourse.

These contraceptive gels are optionally packaged in single-dose-unit containers. The pre-measured single-dose units further protect the vagina by eliminating excessive and potentially irritative overdosing associated with traditional methods of application. The packaging also preserves the sterility and stability of the composition until the moment of use.

For added protection against conception and transmission of sexually transmitted disease, each dosage is applied in combination with a female mechanical barrier-type device. A preferred device is the Femcap® feminine cap described in U.S. Pat. Nos. 4,858,624, 4,989,618, and 5,207,232. (Femcap®, INC. P.O. Box 2236, Del Mar, Calif. 92014-1536.) This device is designed with a "bowl" that covers the cervix to block or shield it from the direct and immediate entry of the ejaculate fluid, enhancing the effects of the microbicidal spermicide. This device is also designed with a "groove" (on the other side of the "bowl," i.e., facing the vaginal opening) that carries or holds the microbicidal spermicide, making it available for continuous release in the vagina. Use of such a mechanical barrier can minimize irritation to and absorption by the vagina of the microbicidal spermicide. It can also function to trap the sperm and microbes and thereby increase their time of exposure to the microbicidal spermicide. This greatly reduces the virulence of invading pathogenic microorganisms resulting in protection against infection by agents of sexually transmitted diseases, and vastly augments the contraception capability.

In operation, the contraceptive gel is applied to the Femcap® feminine cap during preparation for insertion. Optionally, a single-dose-unit is provided prepackaged in a container having a volume of approximately 4–8 ml, optimally about 5 ml. A small amount (⅕ to ½ of a dosage) is first applied to the "bowl" of the Femcap® feminine cap. The remainder of the dosage is then applied in the "groove." Next, this gel is spread in a thin layer all over the cap. The cap is then inserted into the vagina. After insertion and immediately before intercourse, the cap is checked to ensure that it covers the cervix.

The Femcap® feminine cap is designed to be inserted up to 42 hours before intercourse. For purposes of contraception, only the one application of spermicide is necessary, that application being during preparation of the cap for insertion. For further protection against sexually transmitted diseases, however, an additional application of microbicidal spermicide should be introduced into the vagina with each additional act of intercourse (and directed toward the "groove"). An applicator such as those known in the art is provided for this purpose. The Femcap® feminine cap should be left in place at least 6 hours after the last act of intercourse.

EXAMPLES

Particular aspects of the invention may be more readily understood by reference to the following examples, which are intended to exemplify the invention, without limiting its scope to the particular exemplified embodiments.

EXAMPLE 1

A vaginal composition combining a spermicidal chemical and a peroxygen compound, and formulated as a gel, was prepared according to the following protocol.

| INGREDIENTS | MANUFACTURER |
| --- | --- |
| NONOXYNOL-9 | GAF (ISP), Wayne, NJ 800/622-4423 |
| HYDROGEN PEROXIDE 50% | FMC, Philadelphia, PA 800/526-3649 |
| GLYCERINE | PROCTOR & GAMBLE Cincinnati, OH 513/626-3701 |
| POLYACRYLAMIDE & | SEPPIC, |

-continued

| | |
|---|---|
| C13–C14 ISOPARAFFIN & LAURETH-7 | Farfield, NJ 201/882-5597 |
| LACTIC ACID | TRI K, Emerson, NJ 800/26-0372 |
| SIMETHICONE | DOW CORNING, Irvine, CA 800/248-2481 |
| POTASSIUM SORBATE | TRI K, same as above |
| METHYL PARABEN | NIPA, Wilmington, DE 302/478-1522 |
| PROPYL PARABEN | NIPA, same as above |

| FORMULA: PERCENTAGE | INGREDIENT |
|---|---|
| 65.0–75.0 | DEIONIZED WATER |
| 0.1–0.5 | POTASSIUM SORBATE |
| 0.1–0.8 | SIMETHICONE |
| 3.00 | NONOXYNOL 9 |
| 15–25.0 | GLYCERINE DOMESTIC |
| 0.1–0.4 | METHYLPARABEN |
| 0.1–0.3 | PROPYLPARABEN |
| 0.5–2.5 | LACTIC ACID 88% |
| 1.30–5.0 | POLYACRYLAMIDE & C13–14 ISOPARAFFIN & LAURETH-7 |
| 3.00 | HYDROGEN PEROXIDE 50% |

DIRECTIONS:
WARNING:
PROTECTIVE EQUIPMENT (EYE GOGGLES, MASK, THICK RUBBER GLOVES) WERE WORN WHEN HANDLING THE HYDROGEN PEROXIDE.

1. Deionized water was charged into a main tank.
2. Potassium sorbate was added and mixed until dissolved. Once dissolved, nonoxynol-9 was added and mixed until dissolved.
3. When they were dissolved, simethicone was added and mixed to help reduce the incorporation of air.
4. The following were heated in a separate tank: Glycerine, methylparaben, and propylparaben were heated to 175° F. They were mixed well until dissolved. Then they were cooled to 90° F.
5. This separate portion was mixed until it was uniformly blended, taking care to avoid the incorporation of air as much as possible.
6. Then the separate portion was added to the main tank, along with hydrogen peroxide. It was mixed slowly, avoiding aeration.
7. Next lactic acid 88% was added and mixed until uniform.
8. Finally, polyacrylamide, C13–14 isoparaffin, and laureth-7 were added and mixed very slowly to avoid aeration until a thick gel formed.

EXAMPLE 2

Accelerated stability studies of a contraceptive gel having 3% nonoxynol-9 and 3% hydrogen peroxide, at pH 3, prepared according to the protocol described in Example 1, was conducted at high temperatures. These studies demonstrated that nonoxynol-9 and hydrogen peroxide were stable and the pH was maintained at the desired level of about 3 for as long as three years. The product remained stable for 30 days at 42° C, which was calculated to be equivalent to 3 years at 25° C.

While the invention has necessarily been described in conjunction with preferred embodiments and specific working examples, one of ordinary skill in the art, after reading the foregoing specification, will be able to effect various changes, substitutions of equivalents, and alterations to the subject matter, without departing from the spirit and scope of the invention. Hence, the invention can be practiced in ways other than those specifically described here. It is therefore intended that any protection granted be limited only by the appended claims and their equivalents.

What is claimed is:

1. A vaginal composition suitable for preventing conception and transmission of sexually transmitted diseases comprising a spermicidal agent and a peroxygen compound, and having a pH wherein the pH is maintained at about 3 or lower.

2. The composition of claim 1 wherein said spermicidal agent is nonoxynol-9.

3. The composition of claim 1 wherein said peroxygen compound is hydrogen peroxide.

4. The composition of claim 1 wherein said spermicidal agent is present at about 3% by weight.

5. The composition of claim 1 wherein said peroxygen compound is present at about 3% by weight.

6. The composition of claim 1 wherein the pH is maintained at about 3 or lower by the addition of lactic acid.

7. The composition of claim 1 wherein said composition is in the form of a gel.

8. The composition of claim 7 wherein the gel is colorless.

9. The composition of claim 1 further comprising glycerin.

10. The composition of claim 9 wherein said glycerin is present from about 15% to 25% by weight.

11. The composition of claim 1 further comprising one or more gelling agents.

12. The composition of claim 11 wherein said gelling agents are polyacrylamide, C13–14 isoparaffin and laureth-7, and said gelling agents are present in total from about 1.0% to 5.0% by weight.

13. The composition of claim 1 further comprising a defoamer.

14. The composition of claim 13 wherein said defoamer is simethicone and said defoamer is present from about 0.1% to 0.8% by weight.

15. The composition of claim 1 further comprising one or more preservatives.

16. The composition of claim 15 wherein said preservatives are potassium sorbate, which is present at from about 0.1% to 0.5% by weight, methylparaben, which is present at from about 0.1% to 0.3% by weight, and propylparaben, which is present at from about 0.1% to 0.3% by weight.

17. The composition of claim 1 wherein said spermicide is nonoxynol-9 at about 3% by weight, and said peroxygen compound is hydrogen peroxide at about 3% by weight, and further comprising the following ingredients by weight: purified water at about 65% to 75%, glycerin at about 15% to 25%, polyacrylamide, C13–14-isoparaffin, and laureth-7 at about 1.0% to 5.0%, lactic acid at about 0.5% to 2.5%, simethicone at about 0.1% to 0.8%, potassium sorbate at about 0.1% to 0.5%, methylparaben at about 0.1% to 0.3%, and propylparaben at about 0.1% to 0.3%.

18. A kit adapted for barrier-type prevention of conception and transmission of sexually transmitted diseases comprising a barrier-type device and the composition of claim 1.

19. A method of preventing conception and transmission of sexually transmitted diseases by applying the composition of claim 1 intravaginally.

* * * * *